(12) United States Patent
Hall et al.

(10) Patent No.: US 9,913,626 B1
(45) Date of Patent: Mar. 13, 2018

(54) EXCRETA-SAMPLING AND CHILLING TOILET

(71) Applicants: David R. Hall, Provo, UT (US); Daryl Wise, Provo, UT (US); Ben Swenson, Lehi, UT (US); Dan Allen, Springville, UT (US); Jared Reynolds, Pleasant Grove, UT (US); Joshua Larsen, Spanish Fork, UT (US); Justin Robinson, Provo, UT (US); Joe Fox, Spanish Fork, UT (US); Kevin Cheatham, Provo, UT (US)

(72) Inventors: David R. Hall, Provo, UT (US); Daryl Wise, Provo, UT (US); Ben Swenson, Lehi, UT (US); Dan Allen, Springville, UT (US); Jared Reynolds, Pleasant Grove, UT (US); Joshua Larsen, Spanish Fork, UT (US); Justin Robinson, Provo, UT (US); Joe Fox, Spanish Fork, UT (US); Kevin Cheatham, Provo, UT (US)

( * ) Notice: Subject to any disclaimer, the term of this patent is extended or adjusted under 35 U.S.C. 154(b) by 0 days.

(21) Appl. No.: 15/248,788

(22) Filed: Aug. 26, 2016

(51) Int. Cl.
*A47K 11/02* (2006.01)
*A61B 10/00* (2006.01)
*A47K 17/00* (2006.01)
*A61B 5/20* (2006.01)

(52) U.S. Cl.
CPC ......... *A61B 10/0038* (2013.01); *A47K 11/02* (2013.01); *A47K 17/00* (2013.01); *A61B 5/207* (2013.01); *A61B 2562/0257* (2013.01)

(58) Field of Classification Search
CPC ........ A61B 10/0038; A47K 17/00; B07C 5/16
USPC .......................... 4/319, 320, DIG. 19; 222/58
See application file for complete search history.

(56) References Cited

U.S. PATENT DOCUMENTS

| | | | | |
|---|---|---|---|---|
| 4,961,431 A | * | 10/1990 | Ikenaga | A61B 5/14507 600/573 |
| 5,073,500 A | * | 12/1991 | Saito | A61B 5/14507 4/300 |
| 5,111,539 A | * | 5/1992 | Hiruta | A61B 5/02241 4/301 |
| 5,218,971 A | * | 6/1993 | Minami | A61B 5/208 235/375 |
| 5,901,385 A | * | 5/1999 | Nian | A47K 11/02 210/532.1 |
| 6,101,641 A | * | 8/2000 | Hawkins | A47K 11/02 4/449 |
| 6,537,262 B2 | * | 3/2003 | Thompson | A61F 5/4556 4/144.2 |
| 6,779,206 B1 | * | 8/2004 | Sykes | A47K 17/00 4/301 |
| 7,014,778 B2 | * | 3/2006 | Fuchigami | A47K 11/023 110/165 R |
| 7,360,259 B2 | * | 4/2008 | Chan | E03D 5/014 4/300.3 |

(Continued)

*Primary Examiner* — Janie Loeppke

(57) ABSTRACT

An excreta-sampling toilet is disclosed which includes a bowl, a processing apparatus, and a chiller. The bowl separates excreta into solid excreta and liquid excreta. The processing apparatus then processes the solid excreta into a solid excreta sample, including metering it by weight or volume and storing it in containers. The chiller lowers the temperature of the sample, which is stored to await analysis. A metered liquid excreta sample is also stored and chilled in separate storage containers.

19 Claims, 12 Drawing Sheets

(56) References Cited

U.S. PATENT DOCUMENTS

2006/0184144 A1* 8/2006 Goulden ............ A61B 10/0038
  604/317
2008/0034899 A1* 2/2008 Kikuiri ............. A61B 10/0038
  73/864.51

* cited by examiner

EXCRETA-SAMPLING AND CHILLING TOILET

TECHNICAL FIELD

This invention relates generally to the field of health data collection devices, and more specifically to utilizing a toilet to collect excreta for analysis.

BACKGROUND

Health data is collected by healthcare professionals and patients for the purpose of understanding and improving patients' health. It is common for physicians to collect this data in clinics and hospitals; however, when necessary, samples of blood, urine, mucus, feces, etc. are collected and sent to a laboratory for further analysis and data collection.

One problem with data collection is that it can be tedious, requiring a patient's time and the time of his or her physician. When a sample is required to be sent to a laboratory, sample collection can be inconvenient for a patient as he or she may need to travel to give the sample. In addition, fecal samples can be unsanitary and/or repulsive to collect and handle. Another problem is that a sample which is collected at one moment in time may be representative of only that moment. In general, when a patient is out of a care facility, data and/or sample collection may not be as frequent or as regular as would be desired to obtain more comprehensive health data.

SUMMARY OF THE INVENTION

An excreta-sampling toilet is disclosed that overcomes or improves upon the limitations discussed above. In general, the excreta-sampling toilet includes a sewer isolation valve, a bowl, a processing apparatus, and a chiller. The bowl separates excreta into solid excreta and liquid excreta. The processing apparatus then processes the solid excreta into a solid excreta sample, including metering it by weight or volume and storing it in containers. The chiller lowers the temperature of the sample, which is stored to await analysis.

The general embodiment described above saves time and may be more convenient for patients and physicians, because the solid excreta sample may be collected automatically in the homes and care facilities of the patients. Due to solid excreta samples being automatically processed and stored in containers, patients and physicians need not collect nor handle the samples directly, making the sample collection more sanitary. Patients with excreta-sampling toilets located in their residences may have the added benefit of more frequent and regular excreta samples, resulting in more comprehensive health data. Additionally, the invention described above cools excreta samples so that they can be reliably tested even after relatively long amounts of time.

In one embodiment, an excreta-sampling toilet is disclosed which includes a sewer isolation valve, a bowl, a processing apparatus, and a chiller. The bowl receives excreta, in which liquid excreta is separated from solid excreta. The processing apparatus includes one or more containers. The processing apparatus processes a metered amount of a solid excreta sample and stores the solid excreta sample in one or more of the containers. The chiller chills the solid excreta sample for disposition and analysis.

BRIEF DESCRIPTION OF THE DRAWINGS

A more particular description of the invention briefly described above is made below by reference to specific embodiments. Several embodiments are depicted in drawings included with this application, in which.

DETAILED DESCRIPTION

A detailed description of the claimed invention is provided below by example, with reference to embodiments in the appended figures. Those of skill in the art will recognize that the components of the invention as described by example in the figures below could be arranged and designed in a wide variety of different configurations. Thus, the detailed description of the embodiments in the figures is merely representative of embodiments of the invention, and is not intended to limit the scope of the invention as claimed.

In some instances, features represented by numerical values, such as dimensions, mass, quantities, and other properties that can be represented numerically, are stated as approximations. Unless otherwise stated, an approximate value means "correct to within 50% of the stated value." Thus, a length of approximately 1 inch should be read "1 inch+/−0.5 inch." In the case of temperature, approximately means "correct to within 1° C. of the stated temperature."

Figure 1A:
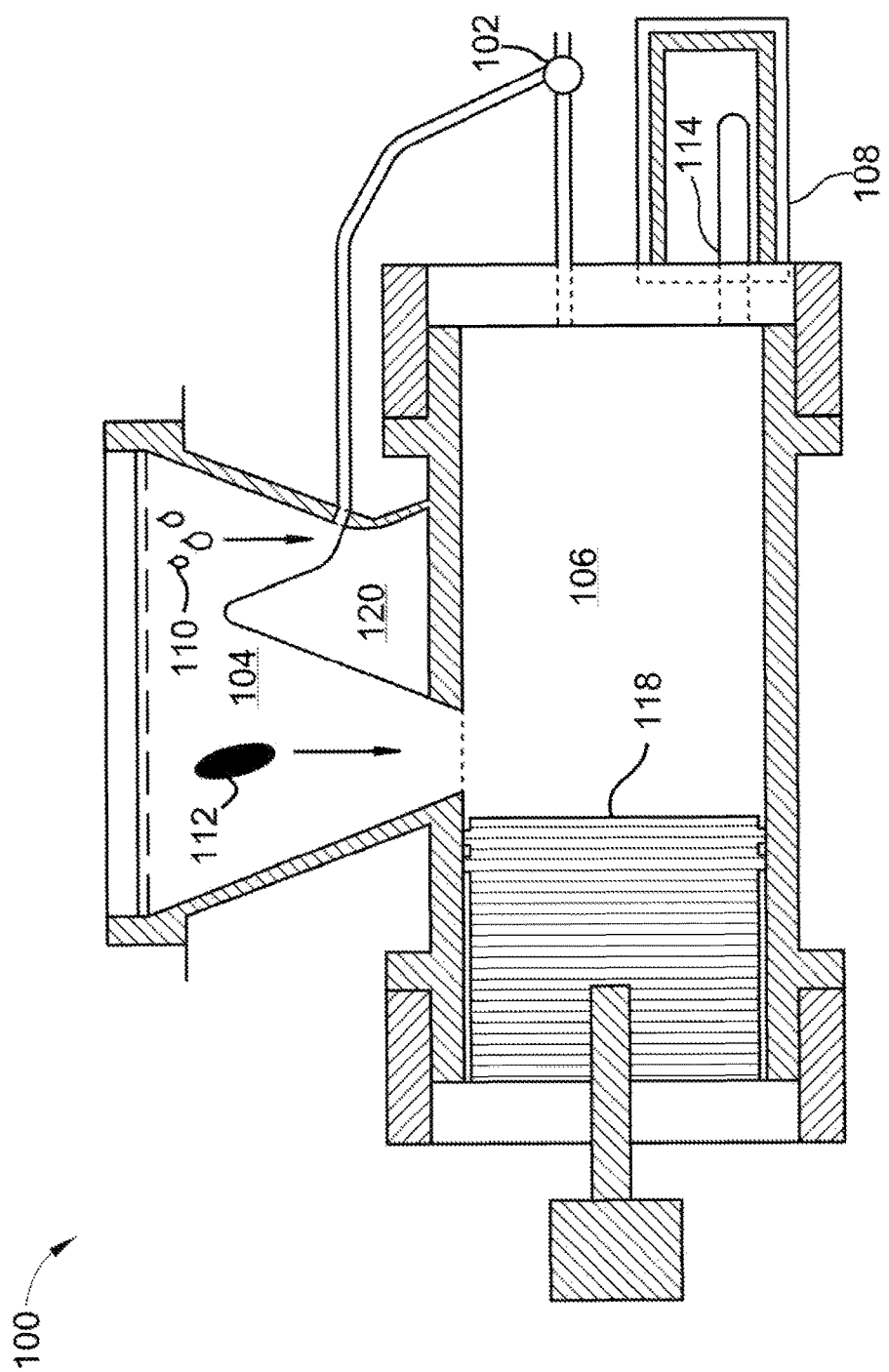
FIG. 1A and FIG. 1B depict a cross-sectional side view of an excreta-sampling toilet.
Figure 1B:
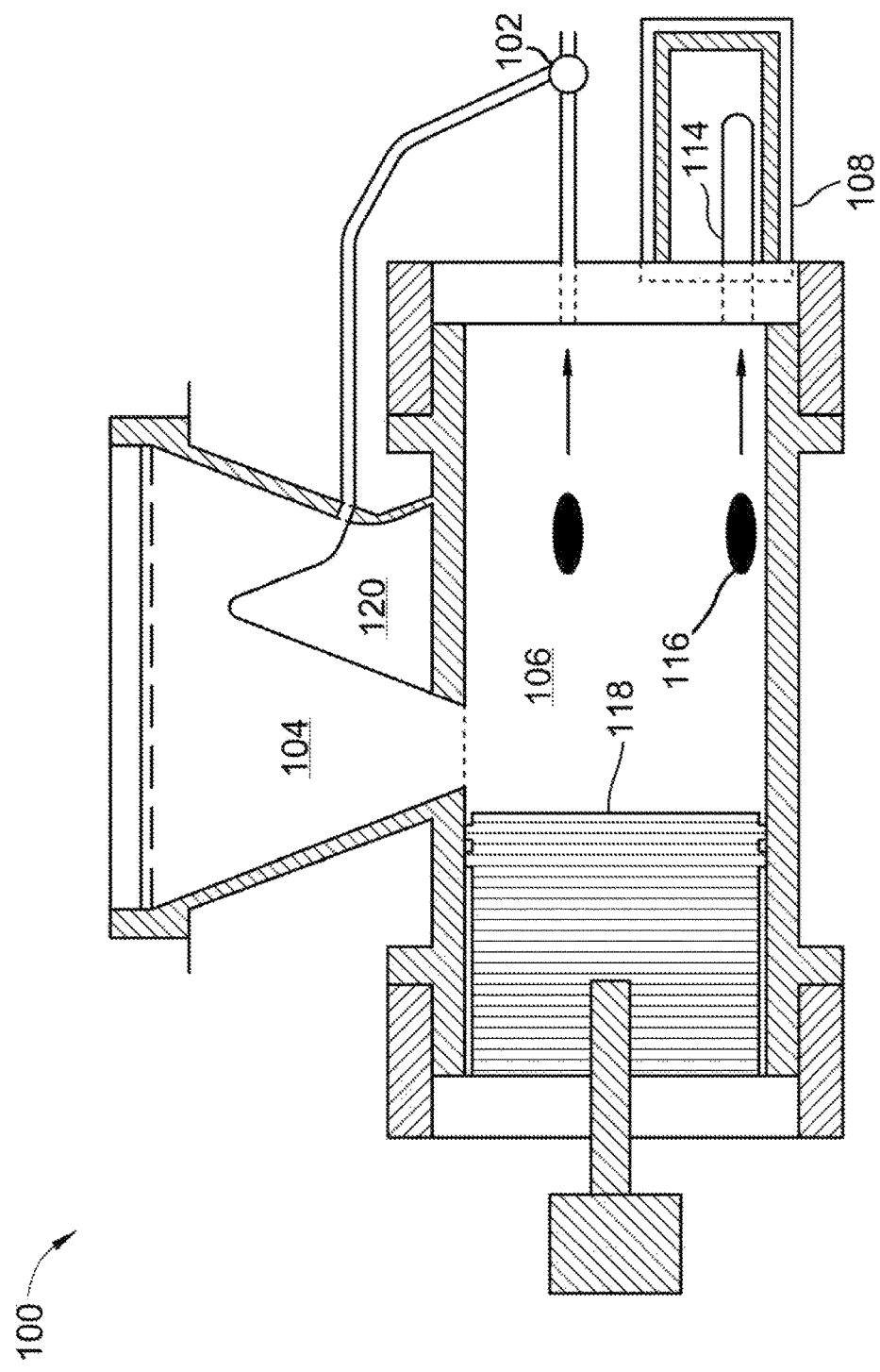

FIG. 1A and FIG. 1B depict a cross-sectional side view of an excreta-sampling toilet. Excreta-sampling toilet 100 includes sewer isolation valve 102, bowl 104, processing apparatus 106, and chiller 108. Bowl 104 receives excreta. Liquid excreta 110 is separated from solid excreta 112 in bowl 104. Processing apparatus 106 includes one or more containers 114. Processing apparatus 106 processes a metered amount of solid excreta sample 116 and stores solid excreta sample 116 in the one or more containers 114. Chiller 108 chills solid excreta sample 116 for disposition and analysis. Solid excreta 112 is moved from bowl 104 to processing apparatus 106. After solid excreta 112 is processed, it may be metered based on volume or weight into a separate constituent. For purposes of this description, the separate constituent of solid excreta 112 described above is defined as solid excreta sample 116. Any solid excreta 112 in excess of the metered amount of solid excreta sample 116 may be removed from processing apparatus 106 through sewer isolation valve 102 and into a sewage waste pipe. Similarly, liquid excreta 110 may be removed from bowl 104 through pipes or tubes, through sewer isolation valve 102, and into the sewage waste pipe to be carried to a waste treatment facility, septic tank, leach field, etc.

In some embodiments, processing apparatus 106 includes a rotating rack holding containers 114 which may be coupled to a rotary encoder or other motorized mechanism which automatically rotates the rack when a metered amount of solid excreta sample 116 is stored in one or more of containers 114. In some other embodiments, processing apparatus 106 includes a magazine holding containers 114, which may automatically detach containers 114 when they are ready with samples and put new containers 114 in their place.

Solid excreta sample 116 is stored inside containers 114. Any containers 114 storing solid excreta sample 116, from a current or previous disposition of excreta, may be stored at a temperature lower than room temperature (room temperature meaning approximately 21° C. or 73° F.) within chiller 108. Chiller 108 may be powered by any of a variety of means, including batteries, power from a power outlet, solar panels, a biogas recovery system, etc. When excreta is newly deposited in bowl 104 of toilet 100, it may have a temperature that is much higher than that of room temperature due to its origin from a body. Freshly excreted excreta may be vital to any laboratory test conducted, because the excreta may not have changed significantly due to bacterial action. This being said, cooling or chilling excreta such as solid excreta sample 116 may significantly limit bacterial growth such that solid excreta sample 116 may be useful for testing in a laboratory.

In some embodiments, for example, chiller 108 is a refrigerator which maintains an interior temperature of approximately 0° C. A user may use toilet 100 to deposit excreta in bowl 104 several times a day. In each instance of disposition of excreta, toilet 100 may store solid excreta sample 116 in one or more containers. At some time each day, or at one or more pickup times each week, all solid excreta samples 116 inside their respective containers 114 may be taken to a laboratory by a messenger such as the user, an assistant, a health care provider, a courier service, etc. Solid excreta samples 116 may then be analyzed and any information regarding solid excreta samples 116 or health of the user may be sent to the user's physician directly, an internet accessible database, the user, a family member or guardian of the user, etc. In cases in which the data is sent to an internet accessible database, the database may be accessed via a peripheral device of the user including a smartphone, a tablet, a laptop, a personal computer, etc. In cases wherein the data is sent to the user's physician, the physician may subsequently make plans for treatment and/or perform further analysis. In some embodiments, the user is a *homo sapiens*. In some other further embodiments, the user is any of a variety of animals including a dog, a cat, a bird, a rodent, a reptile, etc. In these embodiments, a top portion of bowl 104 may include a grate or slats for the user to be placed on while depositing excreta in bowl 104.

In some embodiments, chiller 108 holds containers 114 which already have solid excreta samples 116. In addition, chiller 108 may be removable, having a power supply to keep solid excreta samples 116 cool. In this way, solid excreta samples 116 may be transported over larger time periods to a laboratory to be analyzed. In some further embodiments, after a first chiller 108 is removed to be taken to a laboratory with solid excreta samples 116 inside first chiller 108, a second chiller is installed in the place of first chiller 108. In yet some other further embodiments, the connections between all chillers 108 and processing apparatus 106 may be such that removing and replacing chillers 108 may take less time than one minute.

In some embodiments, chiller 108 is a freezer which maintains an interior temperature of −10° C. (14° F.) or less. In some further embodiments, chiller 108 is a thermoelectric cooler. In some other embodiments, chiller 108 is an evacuated freezer.

In some embodiments, heat which is pumped from an interior of chiller 108 may be pumped in part or completely to coils within a toilet seat included in toilet 100. In this way, although chiller 108 may be kept at a low temperature relative to room temperature, the toilet seat of toilet 100 may be warmed.

In some embodiments, processing apparatus 106 includes piston 118. Piston 118 may displace solid excreta 112 within processing apparatus 106. Piston 118 may include a power source such as batteries, connection to a power outlet, solar panels, etc. In some further embodiments, processing apparatus 106 further includes a cylinder has a closed end. Piston 118 is positioned inside the cylinder and is oriented coaxial with the cylinder, and its sides are positioned coincident with interior walls of the cylinder. Piston 118 is positioned such that it may slide along its axis, which is shared with the cylinder, while maintaining a fluid seal. Piston 118 may exert a force on solid excreta 112 as piston 118 slides from one end of the cylinder to another. When piston 118 pushes solid excreta 112 against the closed end of the cylinder, solid excreta 112 may deform until a certain volume of it is extruded into one or more of containers 114. The rest of solid excreta 112 may be forced through valve 102 and into a sewage waste pipe. In this way, the volume inside containers 114 may determine the volume of solid excreta sample 116.

In some embodiments, processing apparatus 106 processes solid excreta sample 116 by chopping, extruding, pulverizing, shearing, smearing or stirring. In some embodiments, for example, processing apparatus 106 includes one or more blades which may be actuated to chop or stir solid excreta 112. In some other embodiments, for example, processing apparatus 106 includes a macerator which may be actuated to pulverize solid excreta 112. In some other embodiments, for example, processing apparatus 106 includes a straight cutting blade which trims solid excreta 112. In some yet other embodiments, for example, processing apparatus 106 includes a punch and die set which blanks a metered amount of solid excreta sample 116 from solid excreta 112.

In some embodiments, solid excreta sample 116 is metered by weight. In some of these embodiments, processing apparatus 106 includes one or more scales. A first scale may be positioned supporting one or more of containers 114 which will receive solid excreta sample 116. A weight difference between empty and partially or completely filled containers 114 may verify a correct weight of solid excreta sample 116 to be stored. A second scale may be positioned underneath where solid excreta 112 may be positioned in processing apparatus 106, such that the second scale may verify a least weight of solid excrement 112 required. If, for example, solid excrement 112 does not have sufficient mass to meet the required weight, the second scale may send signals to a controller, which is coupled to the second scale. The controller may send a signal to a valve or gate contained within processing apparatus 106 to close such that no solid excreta may enter any of containers 114.

In some embodiments, bowl 104 includes a means for separating liquid excreta from solid excreta. Solid excreta and liquid excreta may be separated from each other by means of a partition 120 which separates liquid excreta 110 from solid excreta 112. The partition 120 may be a moveable partition. The partition 120 may be connected to a motor and a thermal imaging system which is able to detect and identify solid excreta from liquid excreta and move partition 120 in order to separate solid excreta from liquid excreta. Additionally, or alternatively, sieve may be used to separate solid excreta from liquid excreta. A user seated on toilet 100 deposits excreta (solid excreta 112 and liquid excreta 110) into bowl 104. Partition 120 may deflect liquid excreta 110 toward a front portion of bowl 104, and partition 120 may also deflect solid excreta 112 toward a back portion of bowl 104. Partition 120 may be positioned such that it is at a midpoint between a user's anus and urethra, for the purpose of separating the user's liquid excreta 110 from his or her solid excreta 112. In some embodiments, the user's anus and urethra are close together. Partition 120 may extend sufficiently close to the user to facilitate separation of liquid excreta 110 from solid excreta 112.

In some further embodiments, partition 120 may translate to different positions depending on a position of a seated user. Data indicating the position of the user's anus and urethra may be obtained by any of a variety of means including user input, photo sensors placed inside bowl 104, ultrasonic sensors, gas sensors, thermal sensors, force sensors, etc. For example, in some embodiments, a user may be seated on toilet 100. Bowl 104 includes one or more infrared sensors, which collect data about a heat distribution of the user, as seen from inside bowl 104. The infrared sensors may collect this data and send it to a controller, which analyzes the data to determine the locations of highest and lowest heat. Based on this information, the controller may send instructions to partition 120 to move forward, move backward, rotate, and/or change elevation of partition 120 for optimum positioning.

In some embodiments, toilet 100 includes one or more thermal sensors which collect heat data from a user. The heat data may then be used to estimate an internal temperature of the user. Heat data may be stored in a database, internal memory of a controller, a peripheral device, etc. for use by the user and/or his or her physician.

In some embodiments, toilet 100 includes a vacuum assisted flush system. In some other embodiments, toilet 100 includes a ventilation system for venting gases along with a negative pressure gradient to keep noxious gases from exiting into a room via bowl 104.

Sewer isolation valve 102 may keep sewer gases from entering through piping into any other portion of toilet 100. Sewer isolation valve 102 is any of a variety of isolation valves including pneumatic, hydraulic, electric, or electro-hydraulic types. In some embodiments, sewer isolation valve 102 is a one-way valve with a flapper or disc.

Figure 2:
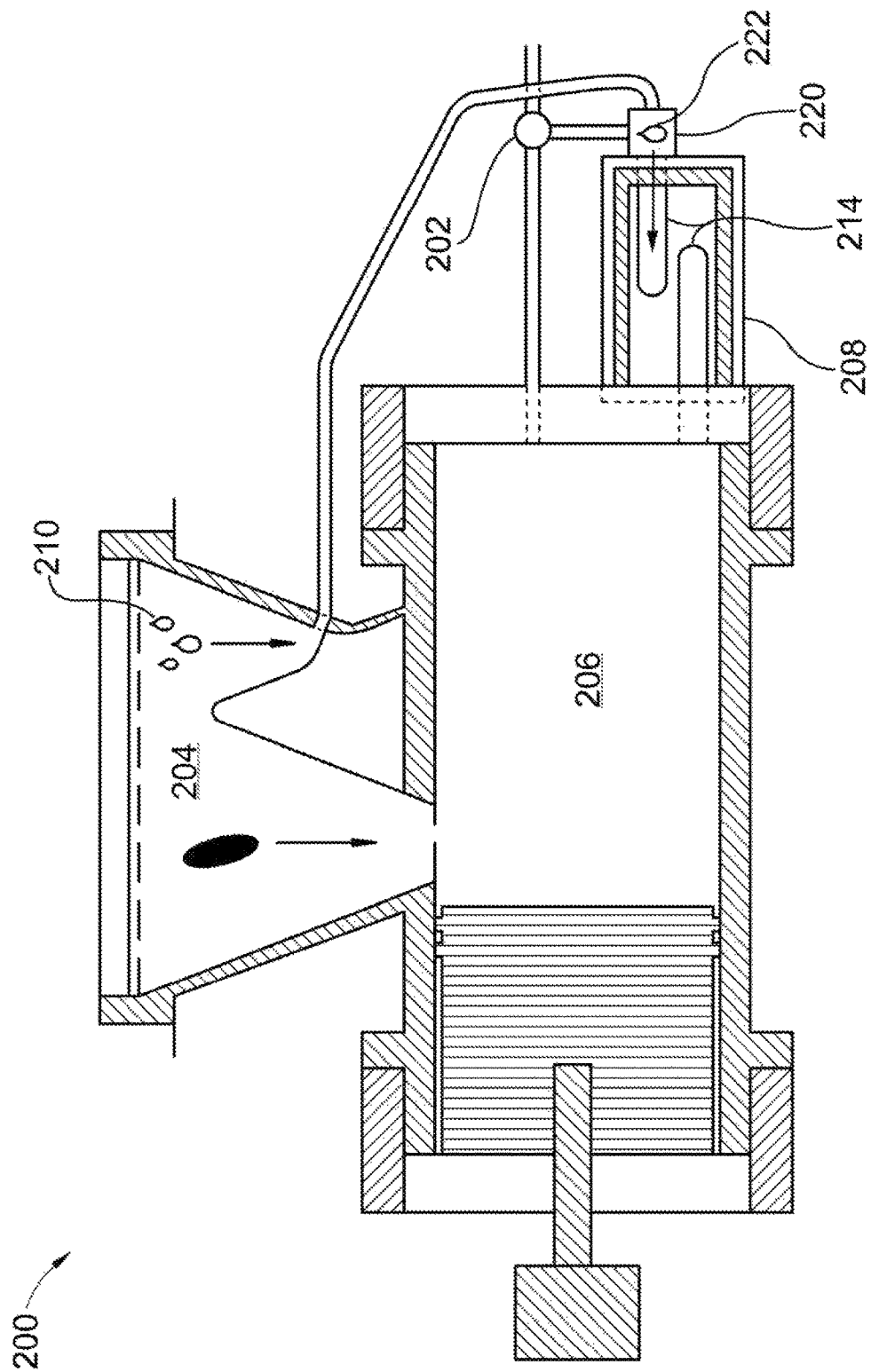
FIG. 2 depicts an embodiment similar to FIG. 1A with an added diverter valve.

FIG. 2 depicts an embodiment similar to FIG. 1A with an added diverter valve. Excreta-sampling toilet 200 includes sewer isolation valve 202, bowl 204, processing apparatus 206, diverter valve 220, and chiller 208. Processing apparatus 206 includes one or more containers 214. Diverter valve 220 fluidly communicates with at least one of containers 214, bowl 204, and sewer isolation valve 202. At least one of containers 214 receives a metered amount of liquid excreta 210, via diverter valve 220, stored as liquid excreta sample 222. When a user deposits liquid excreta 210 into bowl 204, liquid excreta 210 may be gravitationally accelerated and travel through pipes or tubes to diverter valve 220. Diverter valve 220 may allow a metered volume of liquid excreta sample 222 to flow into one of containers 214. After one of containers 214 is full of liquid excreta sample 222, diverter valve 220 may allow any remaining liquid excreta 210 to flow through sewer isolation valve 202. Sewer isolation valve 202 may subsequently allow remaining liquid excreta 210 to flow into a sewer waste pipe to be disposed of.

Figure 3:
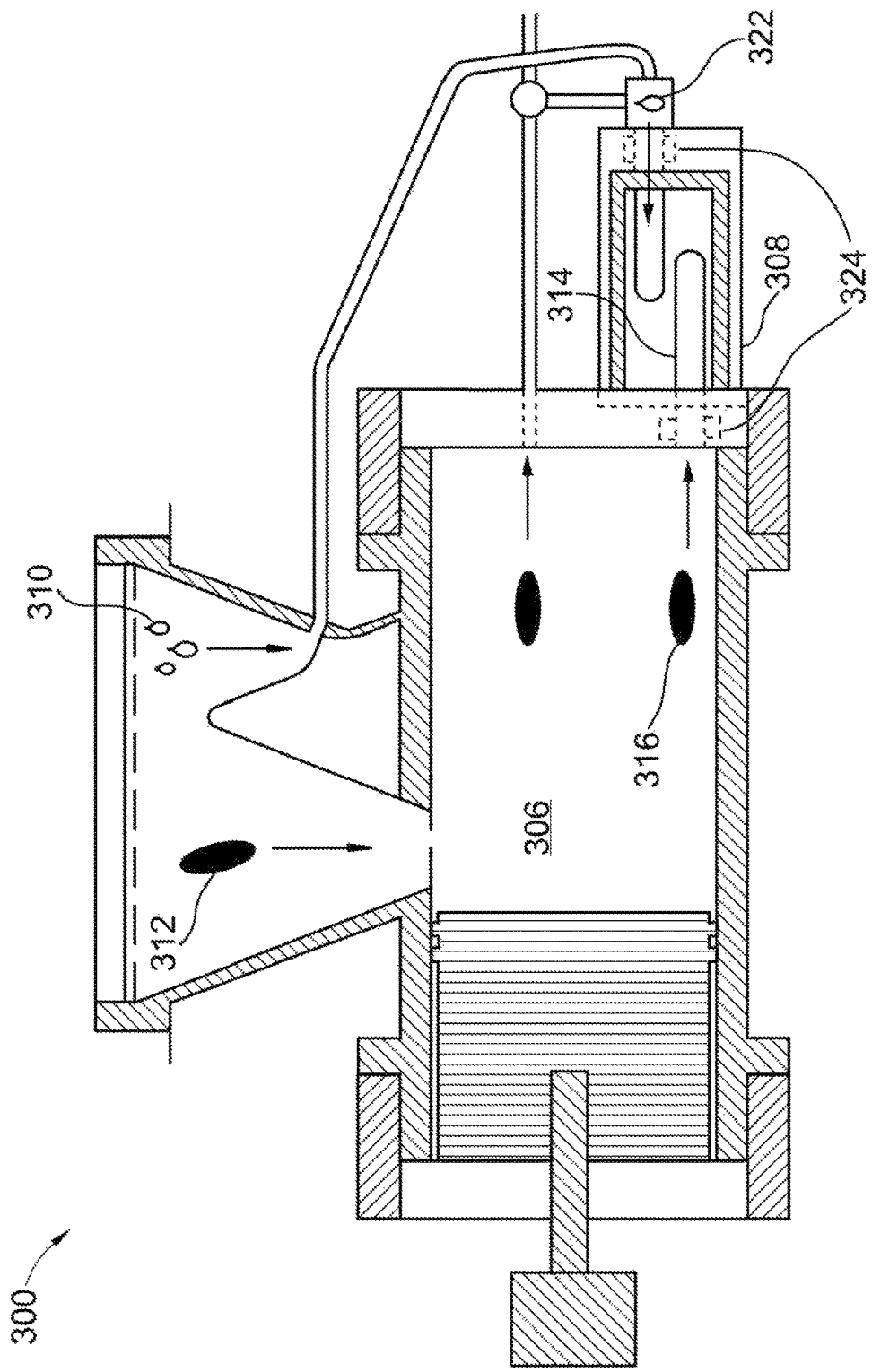
FIG. 3 depicts an embodiment similar to FIG. 2 with added sensors.

FIG. 3 depicts an embodiment similar to FIG. 2 with added sensors. Excreta-sampling toilet 300 includes processing apparatus 306, chiller 308, and one or more sensors 324. Processing apparatus 306 includes one or more containers 314. The one or more sensors 324 may be used to analyze solid excreta 312 and liquid excreta 310. For example, in some embodiments, sensors 324 are sets of capacitive plates which may be positioned around the entrances to containers 314. Capacitances between each set of plates may vary with density and conductive properties of solid excreta 312 or liquid excreta 310. The capacitive plates may be coupled to circuitry including a controller. The controller may record the values of the capacitances. In some other embodiments, sensors 324 may include chemical composition test strips. The test strips may check for pregnancy in a female user by testing liquid excreta 310 for the presence of a beta subunit of human chorionic gonadotropin (hCG). hCG can be detected in urine or blood after implantation, which occurs six to twelve days after fertilization. In some further embodiments, if the test strips included in sensors 324 test positive for hCG, a controller coupled to sensors 324 may send a notification via a wireless transceiver to a peripheral device such as a smartphone, tablet, or laptop.

In some embodiments, sensors 324 indicate receipt of solid excreta sample 316 or liquid excreta sample 322 into containers 314. Sensors 324 may be any of a variety of sensors including active optical proximity sensors, gas sensors, impedance sensors, load sensors, temperature sensors, or ultrasonic proximity sensors.

Figure 4A:
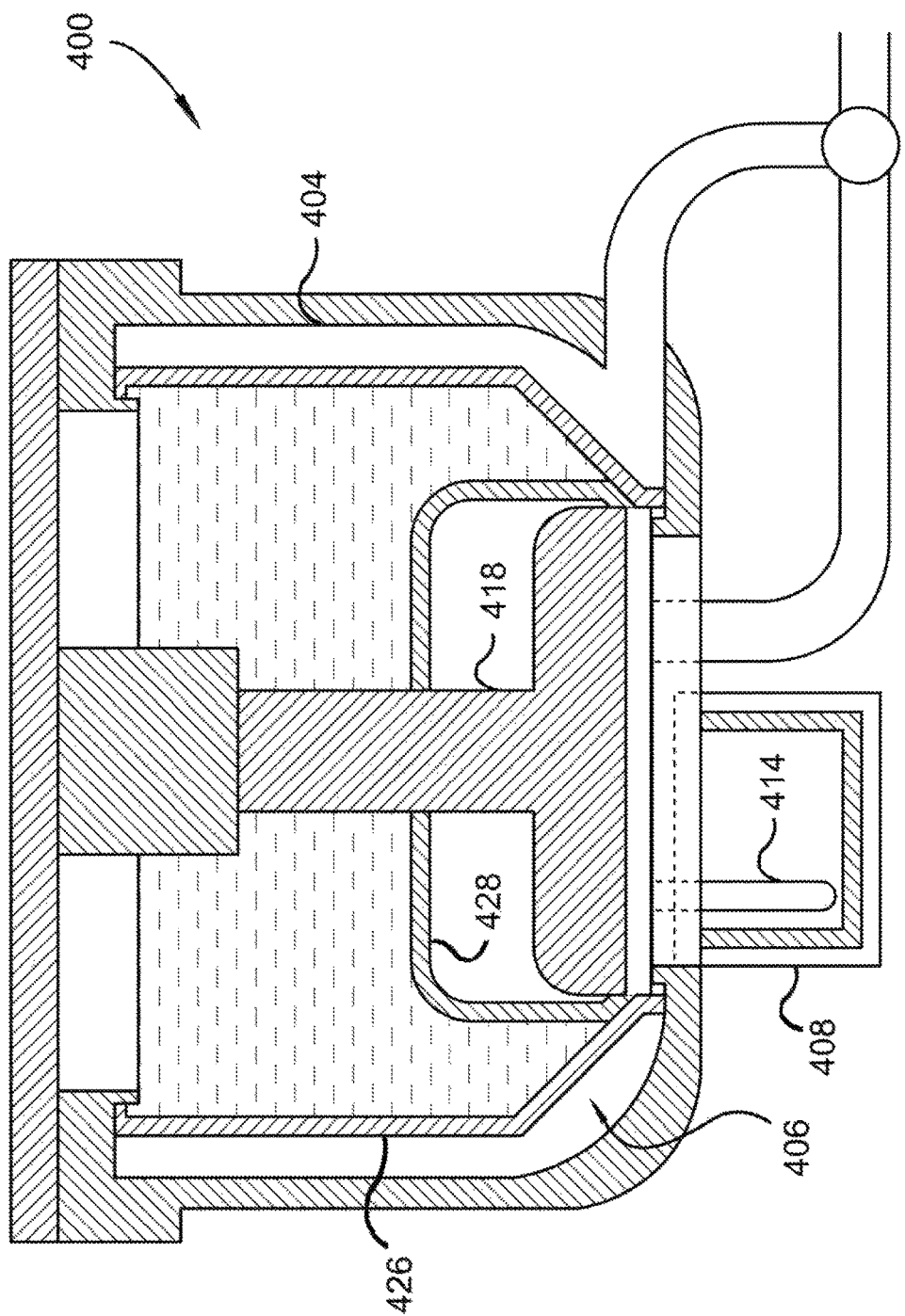
FIG. 4A and FIG. 4B depict an excreta-sampling toilet utilizing a centrifuge.
Figure 4B:
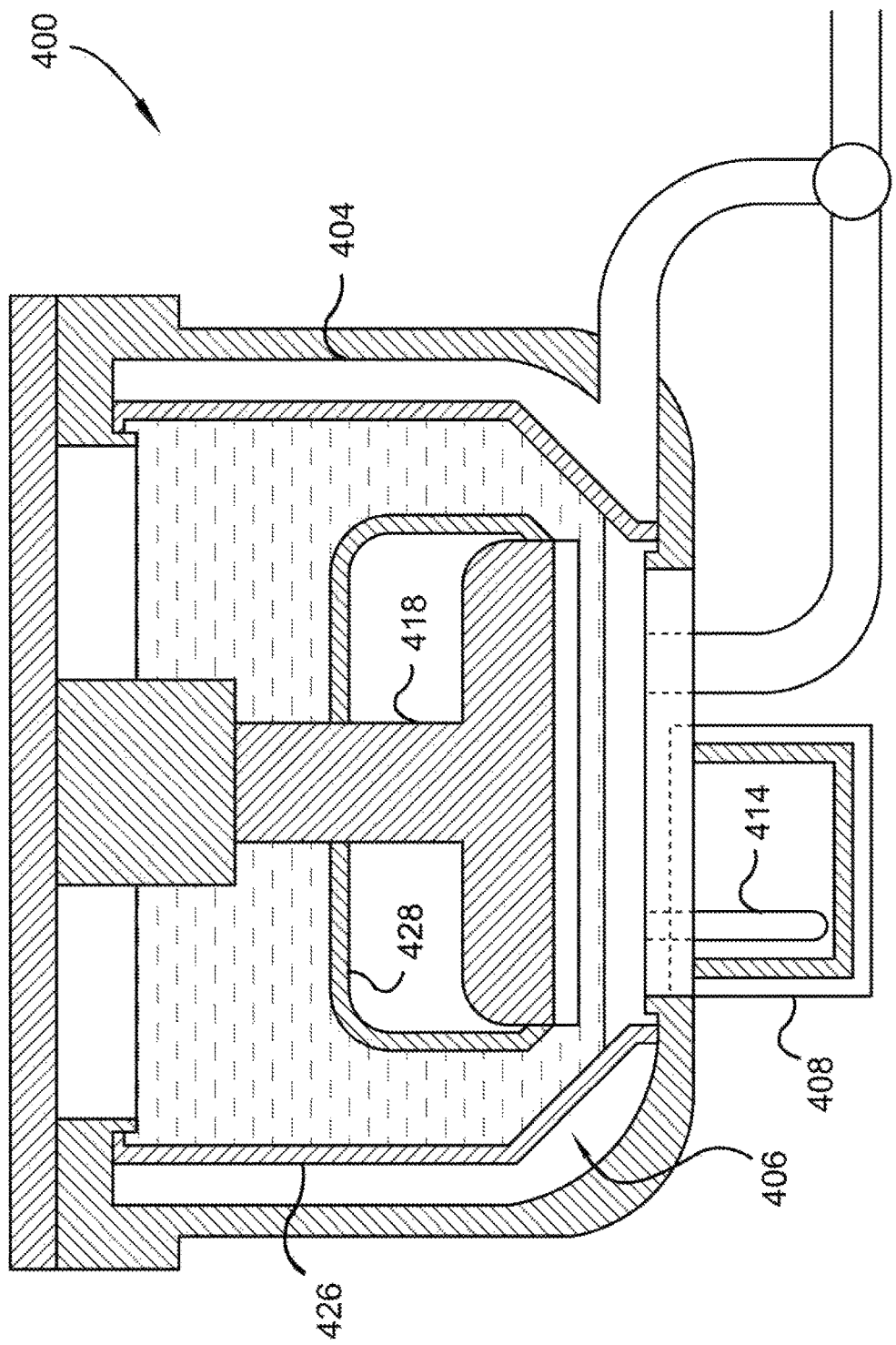

FIG. 4A and FIG. 4B depict an excreta-sampling toilet utilizing a centrifuge. Toilet 400 includes bowl 404, processing apparatus 406, and chiller 408. Processing apparatus 406 includes a centrifuge, one or more containers 414, piston 418, and piston housing 428. The centrifuge includes a centrifugal perforated basket 426 and a centrifugal motor (not shown). Piston 418 may start in a downward position, as shown in FIG. 4A, when excrement is deposited into bowl 404; this is so that excreta cannot enter containers 414 prior to processing. The centrifugal motor may subsequently be actuated, which spins basket 426. As shown in FIG. 4A, piston housing 428 is resting on basket 426 such that friction between piston housing 428 and basket 426 causes piston housing 428 to spin in the same rotational direction as basket 426. Due to piston housing 428 and basket 426 spinning, the deposited excreta may move toward sides of basket 426. Continued spinning of basket 426 may separate liquid excreta, as it moves through perforations in basket 426, from solid excreta, as it cannot pass through the perforations. After the solid and liquid excreta are separated from each other, the liquid excreta may flow into a sewer pipe and piston 418 may lift to allow solid excreta below it, as shown in FIG. 4B. Subsequently, piston 418 may press the solid excreta against a bottom portion of processing apparatus 406 such that a metered amount of the solid excreta sample is pressed into one or more of containers 414. As piston 418 continues to press the solid excreta, any solid excreta in excess of the solid excreta sample may be pushed out of processing apparatus 406 into the sewer pipe. The solid excreta sample and its one or more containers 414 may be cooled by chiller 408 to preserve the solid excreta sample.

Figure 5:
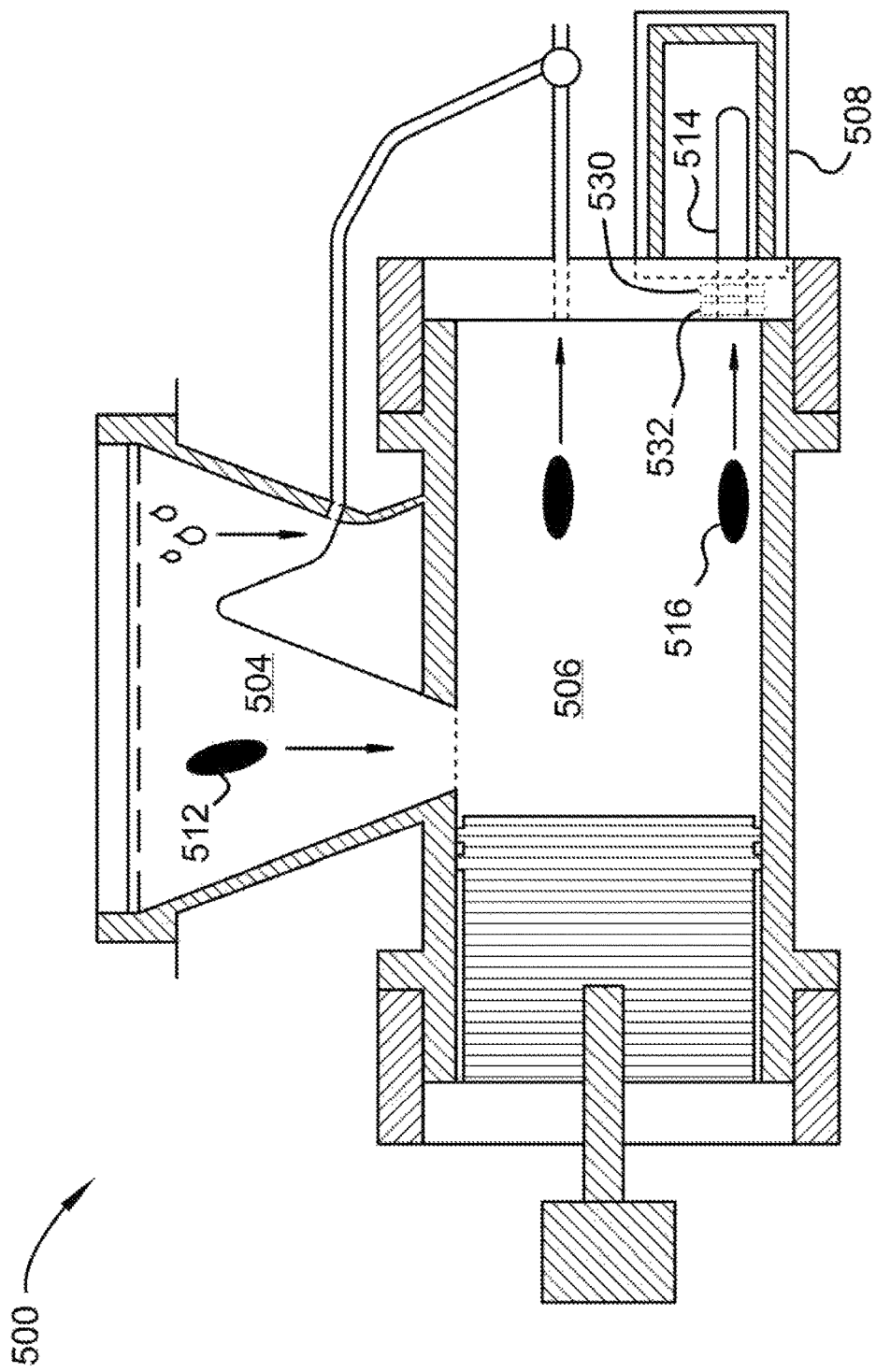
FIG. 5 depicts an embodiment similar to FIG. 1 with added sealing and labeling mechanisms.

FIG. 5 depicts an embodiment similar to FIG. 1 with added sealing and labeling mechanisms. Excreta-sampling toilet 500 includes bowl 504, processing apparatus 506, and chiller 508. Processing apparatus 506 includes one or more containers 514, labeler 530, and sealing mechanism 532. Labeler 530 includes labels. When processing apparatus 506 processes solid excreta sample 516, from solid excreta 512 deposited in bowl 504, processing apparatus 506 may then store solid excreta sample 516 in one or more containers 514. When solid excreta sample 516 is stored in one of containers 514, labeler 530 may automatically label the corresponding container 514 and sealing mechanism 532 may automatically seal the corresponding container 514. For example, in some embodiments, labeler 530 includes partially or completely preprinted labels. Labeler 530 may place one of the labels on each of containers 514 when it has solid excreta sample 516 stored in it. In some further embodiments, labeler 530 may print a date, a time, a QR code, and/or other information related to solid excreta sample 516 on a label which may have been placed on one of containers 514. For example, in a further embodiment, toilet 500 includes sensors which may receive user identifying data and a controller which may send commands to labeler 530 to print a corresponding user's name on a label to be placed on one of containers 514. Respective container 514 may store solid excreta sample 516 derived from the corresponding user. In some embodiments, processing apparatus 506 includes sensors, which may be located in chiller 508, which detect when solid excreta sample 516 is received. These may signal labeler 530 and sealing mechanism 532 to actuate.

In some embodiments, sealing mechanism 532 includes any of a variety of plugs including rubber plugs, plastic caps, wax plugs, etc. In some other embodiments, sealing mechanism 532 includes a heat sealer, wherein containers 514 are plastic bags which are heat sealable.

Figure 6:
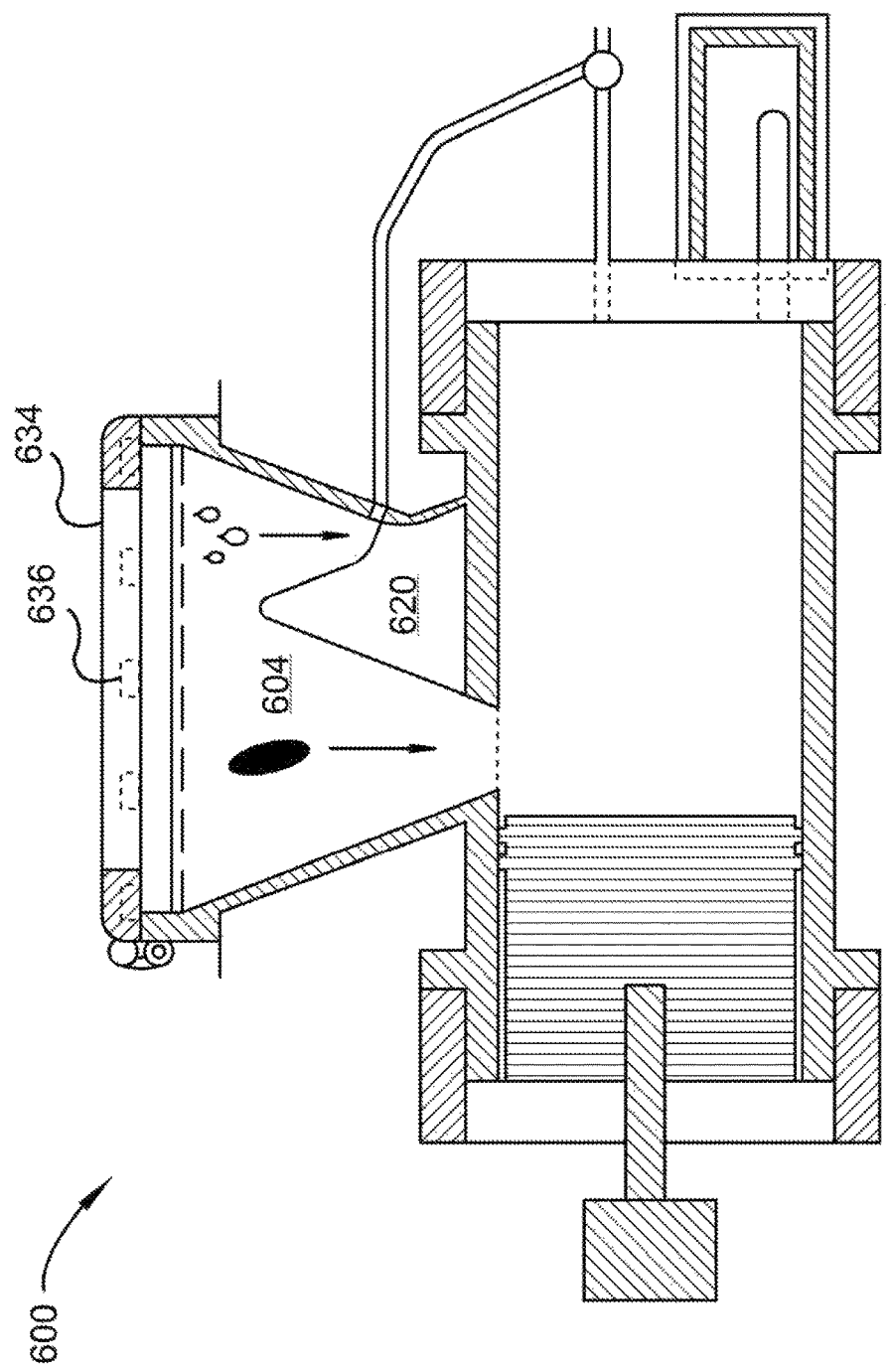
FIG. 6 depicts an embodiment similar to FIG. 1A with an added seat.

FIG. 6 depicts an embodiment similar to FIG. 1A with an added seat. Toilet 600 includes bowl 604 and seat 634. Seat 634 has one or more force sensors 636. Seat 634 may be positioned on bowl 604. Force sensors 636 may be positioned at intervals around seat 634 such that force concentration information may be gathered. For example, in some other embodiments, bowl 604 includes partition 620, wherein partition 620 may move automatically depending on stress concentration information about a user seated on seat 634. Stress concentration information may indicate a user's position on seat 634. In some embodiments, force sensors 636 may measure a user's weight for tracking purposes, and his or her weight may be stored in a database, internal memory of a controller, a peripheral device, etc.

Figure 7:
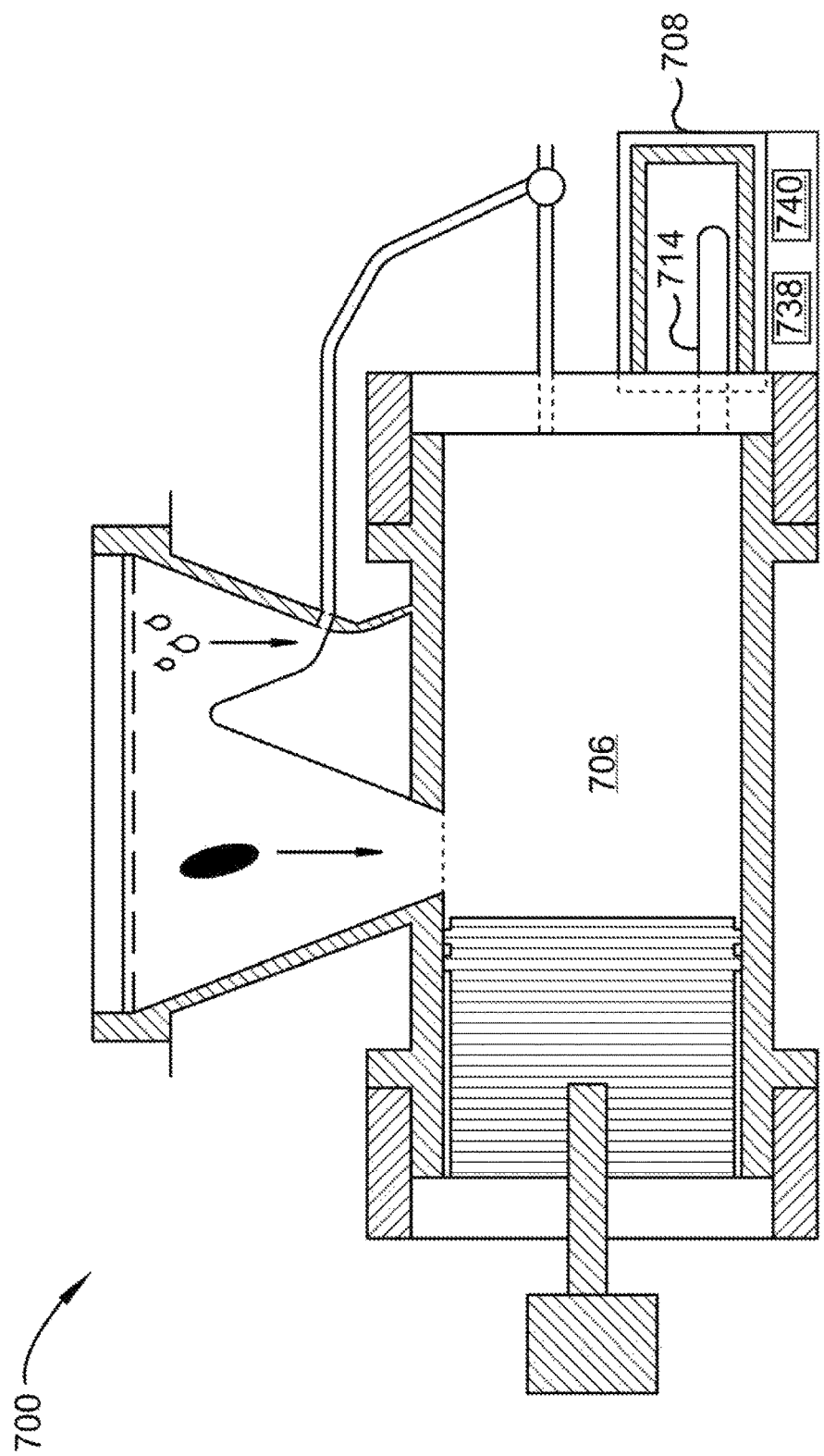
FIG. 7 depicts an embodiment similar to FIG. 1A with added controller and transceiver.

FIG. 7 depicts an embodiment similar to FIG. 1A with added controller and transceiver. Excreta-sampling toilet 700 includes controller 738, wireless transceiver 740, processing apparatus 706, and chiller 708. Processing apparatus 706 includes one or more containers 714. Controller 738 may store and send instructions to processing apparatus 706 to direct it to actuate and to change its processes and settings at different times. For example, in some embodiments, toilet 700 includes sensors for analyzing liquid and solid excreta. One of the sensors may detect hGC (described above) in liquid excreta deposited by a user. Controller 738 may store instructions to only check for hGC at certain times of day or for specific users. Controller 738 may receive instructions via transceiver 740 from a peripheral device of a user or her physician. This may save power, time, and resources, such as chemical test strips, when the sensor is instructed not to actuate or test for hGC. This may similarly be done with other sensors. In some further embodiments, the one or more sensors include chemical test strips.

In some embodiments, processing apparatus 706 includes sensors which may send signals to controller 738 when a solid excreta sample is received by one of containers 714. Controller 738 may send instructions via transceiver 740 to a courier service and a laboratory technician to alert them that the sample is ready to be retrieved and tested.

Figure 8:
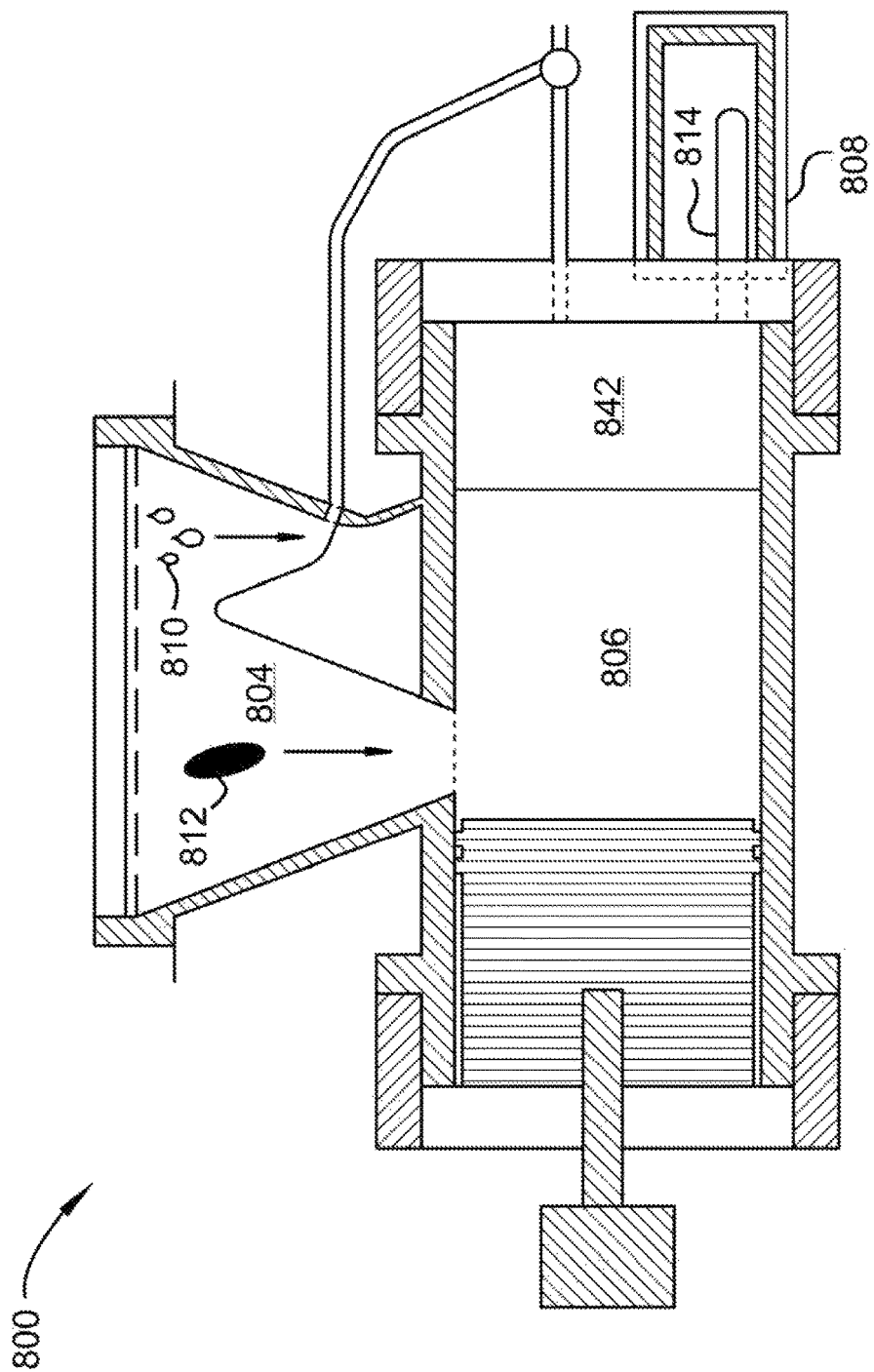
FIG. 8 depicts an embodiment similar to FIG. 1A with an added dryer.

FIG. 8 depicts an embodiment similar to FIG. 1A with an added dryer. Excreta-sampling toilet 800 includes processing apparatus 806, bowl 804, and chiller 808. Processing apparatus 806 includes one or more containers 814 and dryer 842. Bowl 804 receives excreta, wherein solid excreta 812 is separated from liquid excreta 810. Processing apparatus 806 receives solid excreta 812. Dryer 842 removes further undesired liquid excreta 810 from solid excreta 812 and may dispose of undesired liquid excreta 810 in a sewage pipe. In some embodiments, dryer 842 includes a permeable membrane. Processing apparatus 806 may apply pressure against solid excreta 812, pressing it up against the permeable membrane, so that the permeable membrane may remove excess moisture. In some other embodiments, dryer 842 includes a centrifuge which spins solid excreta 812 to remove excess moisture. In some other embodiments, dryer 842 includes a vacuum system positioned partially or completely inside chiller 808. The vacuum system may evacuate a space containing solid excreta 812 within processing apparatus 806 while chiller 808 freezes solid excreta 812 simultaneously. When solid excreta 812 is frozen, with the vacuum system still actuated, solid excreta 812 may be allowed to warm up. While it warms, solid excreta 812 may release moisture into the evacuated space. The vacuum system may remove the additional moisture. In this way, dryer 842 may "freeze dry" solid excreta 812, and processing apparatus 806 may subsequently process a metered amount of a solid excreta sample and store it in one or more of containers 814.

Figure 9:
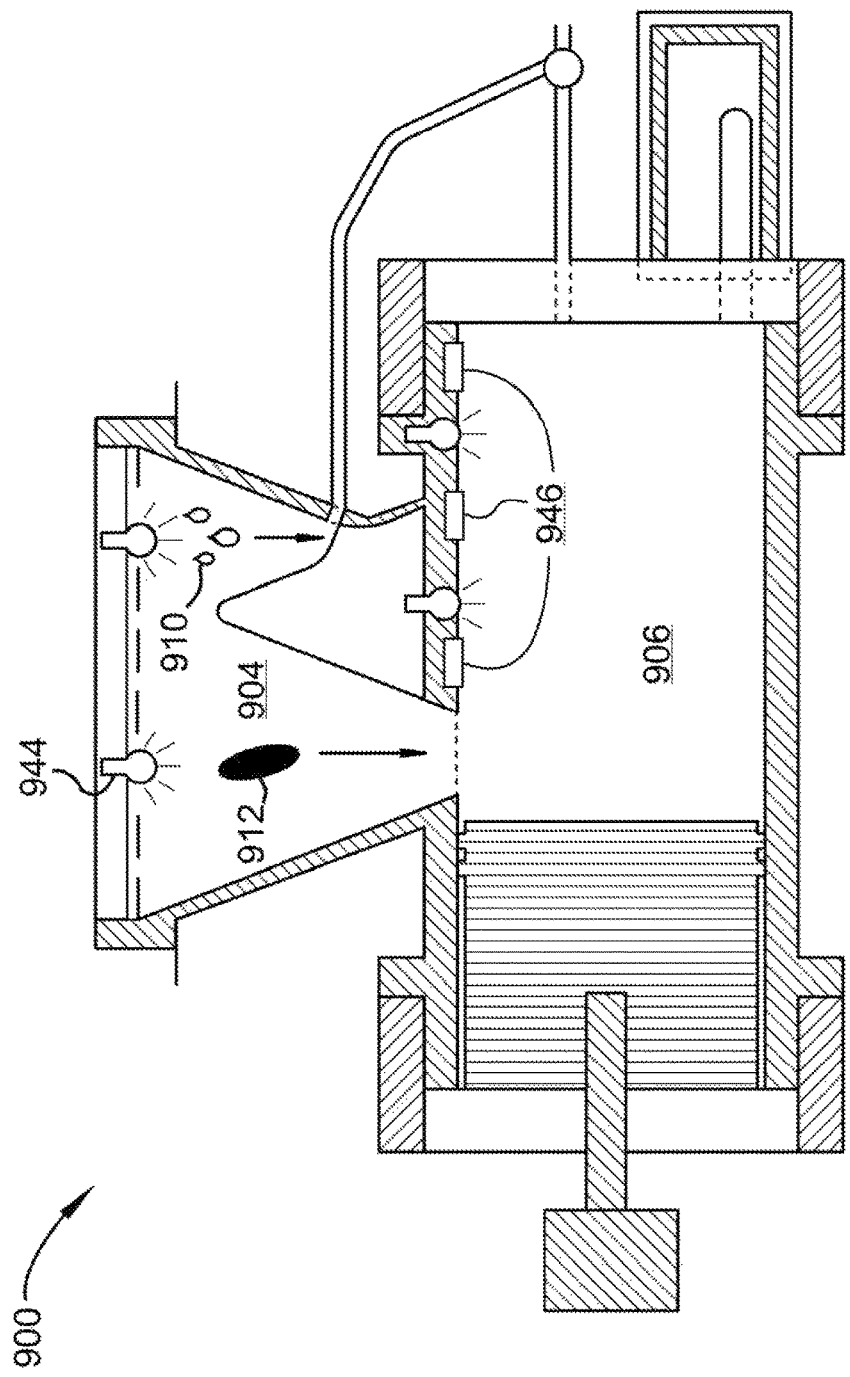
FIG. 9 depicts an embodiment similar to FIG. 1A with added light transmitters and receivers.

FIG. 9 depicts an embodiment similar to FIG. 1A with added light transmitters and receivers. Excreta-sampling toilet 900 includes bowl 904, processing apparatus 906, one or more light transmitters 944, and one or more light receivers 946. Bowl 904 receives excreta, wherein liquid excreta 910 is separated from solid excreta 912. Light transmitters 944 may emit wavelengths of light that partially sanitize and impede bacterial growth, such as ultraviolet, x-ray, and gamma wavelengths of light. Light receivers 946 may meter bacterial growth by receiving light wavelengths corresponding to light emitted from a chemical reaction with adenosine triphosphate (ATP). ATP is a molecule that may be found in and around living cells, and it may give a direct measure of biological concentration. ATP may be quantified by measuring light produced through its reaction with a naturally occurring firefly enzyme, luciferase, using light receivers 946. An amount of light produced may be directly proportional to an amount of ATP present. In some embodiments, an amount of bacterial growth detected via light receivers 946 may be directly proportional to an intensity of light emitted by light transmitters 944 to further impede bacterial growth. In some other embodiments, toilet 900 includes a light emitter which is coupled to light transmitters 944, wherein light transmitters 944 are optical fiber cables. In some embodiments, luciferase is injected into toilet 900 in order to measure light produced through its reaction with ATP.

Figure 10:
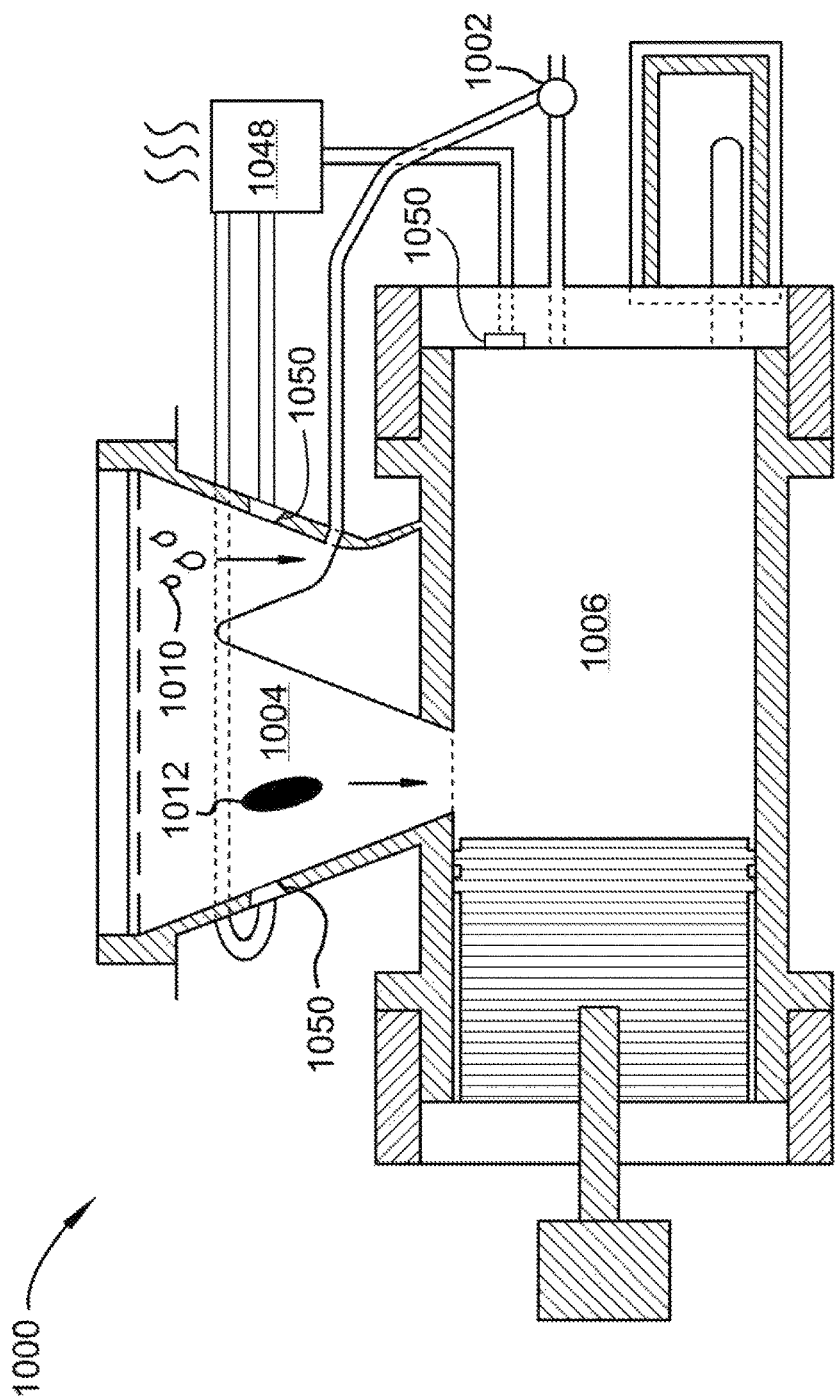
FIG. 10 depicts an embodiment similar to FIG. 1A with added cleaning solution sprayer.

FIG. 10 depicts an embodiment similar to FIG. 1A with added cleaning solution sprayer. Excreta-sampling toilet 1000 includes sewer isolation valve 1002, bowl 1004, processing apparatus 1006, and cleaning sprayer 1048. Toilet 1000 may need to be sanitized regularly in order to collect good samples of solid excreta 1012 and liquid excreta 1010. Cleaning sprayer 1048 injects a super-heated cleaning solution to clean toilet 1000. In the depicted embodiment, cleaning sprayer 1048 includes multiple nozzles 1050.

Nozzles 1050 may be positioned on interior walls of bowl 1004 and processing apparatus 1006. When actuated, cleaning sprayer 1048 injects the super-heated cleaning solution via nozzles 1050. After toilet 1000 is sufficiently cleaned, any remaining cleaning solution which has not already exited toilet 1000 via sewer isolation valve 1002 into a sewage waste pipe is removed from the system by any of a variety of means including a vacuum, a desiccating agent, a heated or non-heated air pump, or a rinse of heated potable water via nozzles 1050.

In some embodiments, nozzles 1050 are rotary nozzles such that every surface within bowl 1004 and processing apparatus 1006 may be impinged upon with cleaning solution. In some embodiments, toilet 1000 includes a lid which covers bowl 1004 such that no cleaning solution may exit toilet 1000 while cleaning sprayer 1048 may be cleaning it.

In some other embodiments, sewer isolation valve 1002 remains closed while toilet 1000 is being cleaned, and sewer isolation valve 1002 may open afterwards. In some further embodiments, when sewer isolation valve 1002 opens, fluids containing cleaning solution, solid excreta 1012, and liquid excreta 1010 within toilet 1000 may empty through sewer isolation valve 1002. The draining of this fluid all at once may result in siphon action.

The invention claimed is:

1. An excreta-sampling toilet comprising:
    a bowl comprising a means for separating liquid excreta from solid excreta;
    a sample metering device connected to the means for separating solid excreta, wherein the sample metering device comprises a scale and wherein the sample metering device meters the solid excreta by weight into a separate constituent;
    a solid excreta processing apparatus comprising a chiller compartment;
    one or more storage containers disposed within the chiller compartment, wherein a metered amount of the solid excreta is stored as a chilled sample within the one or more storage containers.

2. The excreta-sampling toilet of claim 1, further comprising a diverter valve which fluidly communicates with at least one of the one or more storage containers and the bowl, wherein at least one of the one or more storage containers receives a metered amount of the liquid excreta, via the diverter valve.

3. The excreta-sampling toilet of claim 2, wherein the metered amount of the liquid excreta is stored as a liquid sample within the chiller compartment.

4. The excreta-sampling toilet of claim 2, further comprising one or more sensors for analyzing the solid excreta and liquid excreta.

5. The excreta-sampling toilet of claim 4, wherein the one or more sensors comprise chemical test strips.

6. The excreta-sampling toilet of claim 1, wherein the solid excreta processing apparatus further comprises a dryer which removes undesired liquid excreta from the solid excreta.

7. The excreta-sampling toilet of claim 6, wherein the dryer comprises a vacuum system.

8. The excreta-sampling toilet of claim 1, wherein the solid excreta processing apparatus comprises a piston.

9. The excreta-sampling toilet of claim 1, further comprising a one-way sewer isolation valve.

10. The excreta-sampling toilet of claim 1, wherein the bowl comprises a partition which separates the liquid excreta from the solid excreta.

11. The excreta-sampling toilet of claim 1, wherein the bowl comprises a centrifuge which separates the liquid excreta from the solid excreta.

12. The excreta-sampling toilet of claim 1, wherein the processing apparatus comprises a labeler which labels the one or more storage containers.

13. The excreta-sampling toilet of claim 1, wherein the processing apparatus comprises a sealing mechanism to seal the one or more storage containers.

14. The excreta-sampling toilet of claim 1, further comprising a seat having one or more force sensors.

15. The excreta-sampling toilet of claim 1, further comprising one or more light transmitters.

16. The excreta-sampling toilet of claim 1, further comprising one or more light receivers.

17. The excreta-sampling toilet of claim 1, further comprising a cleaning sprayer which injects a super-heated cleaning solution to clean the excreta-sampling toilet.

18. The excreta-sampling toilet of claim 1, further comprising one or more sensors indicating receipt of the solid excreta sample into the containers, the sensors being active optical proximity sensors, gas sensors, impedance sensors, load sensors, temperature sensors, or ultrasonic proximity sensors.

19. The excreta-sampling toilet of claim 1, wherein the processing apparatus processes the solid excreta sample by chopping, extruding, pulverizing, shearing, smearing, or stirring.

* * * * *